United States Patent

Wlassics et al.

[11] Patent Number: 5,910,587
[45] Date of Patent: Jun. 8, 1999

[54] COMPOUNDS CONTAINING TRIAZINE RING

[75] Inventors: Ivan Wlassics, Genoa; Walter Navarrini, Milan, both of Italy

[73] Assignee: Ausimont S.p.A., Milan, Italy

[21] Appl. No.: 09/028,771

[22] Filed: Feb. 24, 1998

[30] Foreign Application Priority Data

Feb. 25, 1997 [IT] Italy .................................. MI97A0400

[51] Int. Cl.⁶ ................................................ C07D 251/24
[52] U.S. Cl. ............................................................. 544/216
[58] Field of Search ............................................... 544/216

[56] References Cited

U.S. PATENT DOCUMENTS

| | | | |
|---|---|---|---|
| 2,981,734 | 4/1961 | Ratz et al. | 544/216 |
| 3,654,237 | 4/1972 | Schuman et al. | 544/216 |
| 3,847,916 | 11/1974 | Kim et al. | 544/216 |
| 4,523,947 | 6/1985 | Szczepanski et al. | 544/216 |

FOREIGN PATENT DOCUMENTS

97/05122 2/1997 European Pat. Off. .

OTHER PUBLICATIONS

Yung K. Kim et al: "The Preparation and Synthetic Utility of ω–(Vinyl)perfluoroalkanecarboxylates", Journal of Organic Chemistry, vol. 34, No. 3, 1969, pp. 602–605.

*Primary Examiner*—Yogendra N. Gupta
*Attorney, Agent, or Firm*—Nikaido Marmelstein Muray & Oram, LLP

[57] ABSTRACT

Triazines having general formula:

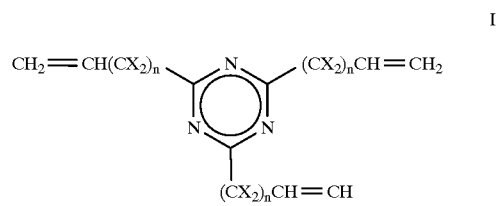

wherein: X can independently be hydrogen, chlorine, fluorine, $C_1$–$C_3$ alkyl or perfluoro alkyl, n is comprised between 2 and 20.

2 Claims, No Drawings

COMPOUNDS CONTAINING TRIAZINE RING

The present invention relates to new compounds containing a triazine ring and the process for their preparation.

The use of compounds containing an isocynuarate ring in the elastomers crosslinkng is known. These compounds, even though they give rise to cured polymers having good rheometric and mechanical characteristics, show the drawback not to be very compatible with the most elastomers and moreover are characterized by a low thermal stability of the isocyanurate ring.

It has been surprisingly founmd by the Applicant that it is possible to synthetize trisubstituted triazines and characterized in that the three substituents contain a terminal double bond. Such compounds not only show a very high thermal stability, but also a high compatibility with the more commonly used elastomers.

In particular the triazines according to the invention have the formula:

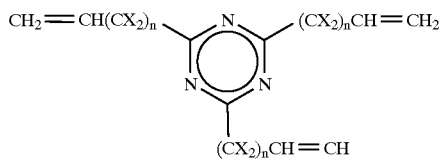

I wherein:

X can independently be hydrogen chlorine, fluorine, $C_1$–$C_3$ alkyl or perfluoroalkyl, n is an integer comprised between 2 and 20, preferably between 4 and 12, more preferably between 4 and 8.

The triazines according to the invention are prepared according to the following process:

a) reaction of a compound of formula I—$(CX_2)_{n+1}$—I, wherein X and n have the above meaning, in the presence of an oxide or of a transition metal salt and of oleum containing an amount of $SO_3$ comprised between 5 and 60% by weight, preferably between 10 and 40% by weight, to give the omega-iodoacylfluoride, b) reaction of the omega-iodoacylfluoride with ammonia to give the corresponding amide, c) reaction of the amide with a dehydrating agent to obtain the corresponding nitrile, d) reaction of nitrile with ammonia at a temperature comprised between –10 and –100° C. to give the corresponding amidine, e) the amidine is condensed at a temperature comprised between 100 and 200° C. to obtain a triazine (Triazine A) characterized by the following formula:

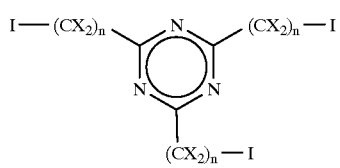

II wherein X and n have the above meanings, f) the triazine A is reacted with ethylene in the presence of an amount of a salt or of a transition metal halide comprised between 1 and 10% by moles based on the triazine A, thus obtaining a triazine (triazine B) having the following formula:

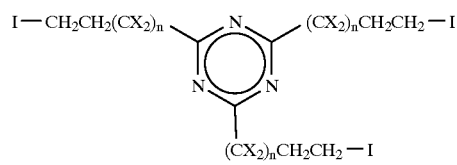

III g) dehydroiodination of the triazine B in basic alcoholic solution to obtain the triazine C of formula I.

In the step a) the catalyst is preferably formed by an Hg or HgO salt; more preferably the catalyst used is $HgSO_4$.

The reaction temperature can range within wide limits, a temperature comprised between 50 and 200° C. is preferred, most preferred between 80 an 150° C.

The reaction time can range within wide limits and depends on the reaction conditions utilized. It is to be noticed that when the reaction time rises, the amount of the obtained diacylfluoride increases, it is therefore advisable to utilize a reaction time between 2 and 12 hours, preferably between 4 and 10 hours.

In step b) of the process an inert solvent is used, such as for instance methylene chloride, ethylic ether, perfluoroheptane or the like. The reaction time can generally range between 10 minutes and 2 hours.

In step c) of the process all the dehydrating agents known in the art such as for instance $P_2O_5$, $SOCl_2$, etc, can be used; preferably $P_2O_5$. The reaction temperature is preferably comprised between 100 and 300° C., more preferably, when X is equal to F, between 120 and 170° C.; the reaction time is generally comprised between 30 minutes and 5 hours.

Step e) of the process is preferably carried out at a temperature comprised between 120 and 170° C. for a time comprised between 2 and 10 hours.

In step f) of the process the reaction is preferably carried out at temperatures comprised between 50 and 250° C., more preferably between 120 and 190° C., in the presence of an excess of ethylene based on the iodine equivalents, preferably the ethylene excess is between 1.05:1 and 5:1.

The pressure is not important for the reaction purposes.

Triazines A and B represent not only compounds for the preparation of the triazines of formula I, but they can be used as such in the elastomers radical polymerization field since they contain iodine.

The process indicated above can be modified for instance by changing the order of some process steps without therefore changing the invention process. It is for instance possible to carry out steps f) and g) (addition of ethylene and dehydroiodination) on an intermediate previous the triazine A instead of on the latter.

The following examples are given for illustrative purposes but are not limitative of the invention.

EXAMPLE 1

Synthesis of 6-iodoperfluorohexanoylfluoride (I-1)

In a 250 ml three necked flask equipped with magnetic stirrer and reflux condenser were reacted: 600 g of an alpha-omega diiodide of formula $I(CF_2)_6I$; 7.14 g of $HgSO_4$ were added as catalyst, equal to about 9% of the diiodide moles. In a dropping funnel connected to the reaction flask 115.8 ml of oleum having a content by weight of $SO_3$ of 34.5%, with an excess of 10% based on the diiodide moles were introduced The flask was heated to 115° C. in a thermostated oil bath. The oleum was added to the reaction flask with a rate of 150 ml/h. The reaction mixture was allowed boiling under reflux for 6 hours, and successively it was distilled at reduced pressure of 13 mbar with a temperature of the oil bath of 88° C. A mixture formed by 92% by moles of monoacylfluoride (I-1) and by 8% by moles of diacylfluoride was obtained.

The conversion of the starting product was of 58% and the total yield of morioacylfluoride was of 53%.

Spectroscopic analyses: FT-IR (NaCl): 1879.2 $cm^{-1}$; 1286 $cm^{-1}$.

$^{19}$F-NMR (90 MHz): −58.5 ppm, s; −83.5 ppm, s; −113 ppm, s; −118.7 ppm, s; −121 ppm, s; −122.7 ppm, S.

EXAMPLE 2

Sintesys of 6-iodoperfluorohexanoylamide (I-2)

244.4 g of I-1, 6-iodoperfluorohexanoylfluoride (0.577 moles) obtained in Example 1, were dissolved in $CH_2Cl_2$ at a temperature of 4° C. The reaction apparatus was the same utilized for the previous synthesis in Example 1.

In the reaction flask $NH_3$ in excess dried on anhydrous $CaCl_2$ was bubbled. The reaction time was 100 minutes (min). The reaction crude product was evaporated at a reduced pressure (26 mbar). 230 g of amide, equal to 0.547 moles, were obtained, with an yield of 95% by moles and having melting point of 131–139° C. and with a thermal resistance such that up to 180° C. the compound does not release $I_2$.

Spectroscopic analyses: FT-IR (KBr): 3420+3200 $cm^{-1}$; 1705 $cm^{-1}$; 1425 $cm^{-1}$; 1200+1180 $cm^{-1}$.

$^{19}$F-NMR (90 MHz in dimethylsulphoxide (DMSO)): −66 ppm, s; −114.1 ppm, s; −118.8 ppm, s; −121.3 ppm, s; −122.7 ppm, s.

EXAMPLE 3

Synthesis of 6-iodoperfluorohexanenitrile (I-3)

213 g of I-2, 6-iodoperfluorohexanoylamide (0.506 moles) obtained in Example 2, were reacted in an one necked flask with 191 g of $P_2O_5$ equal to a molar ratio 8:1 based on the I-2.

I-3 was isolated by distillation at a reduced pressure (8 mbar) at a temperature of 96° C. 75 ml equal to 147 g of I-3 were collected, which appeared as a violet liquid. The conversion of I-2 was of 97% and the yield of the converted product was of 72%.

Spectroscopic analyses: FT-IR (NaCl): 2263 $cm^{-1}$; 1205+1140 $cm^{-1}$;

$^{19}$F-NMR (200 MHz): −59 ppm, s; −105 ppm, s; −112.5 ppm, s; −119.7 ppm, s; −121.7 ppm, s.

EXAMPLE 4

Synthesis of 6-iodoperfluorohexaneamidine (I-4)

147 g of I-3, 6-iodoperfluorohexanenitrile (0.365 moles) obtained from Example 3, were introduced in a 250 ml three necked flask equipped with a reflux condenser. The flask was put in a Dewar containing dry ice/acetone at −80° C. In the reaction flask about 20 ml of liquid ammonia equal to about 0.96 moles with a molar excess of 2.6:1 based on the starting I-3 were condensed. At the end of the ammonia condensation the reaction mixture was heated, under stirring at −30° C., maintaining the mixture at this temperature for 20 min. Successively the reaction mixture was cooled to room temperature. 144.9 g (0.345 moles) of I-4, with a conversion of I-3 of 95% and a yield on the converted product of 99%, were obtained.

Spectroscopic analyses: FT-IR (KBr): 3390+3325 $cm^{-1}$; 1660 $cm^{-1}$; 1620 $cm^{-1}$; 1200+1135 $cm^{-1}$;

$^{19}$F-NMR (90 MHz in acetone): −63.1 ppm, s; −113.5 ppm, s; −117.4 ppm, S; −120.6 ppm, s; −121.7 ppm, S.

EXAMPLE 5 (triazine A)

Synthesis of 2,4,6-(5-iodo-decafluoropentane)[1,3,5] triazine

In an one necked flask 144.9 g of I-4, 6-iodoperfluorohexaneamidine obtained from Example 4, equal to 0.345 moles were introduced and it was heated, under stirring, at 157° C. for 8 hours at atmospheric pressure under $N_2$ atmosphere. The triazine formation (triazine A of formula II) was detectable by the viscosity increase of the reaction mixture and by the light yellow coloring. The reaction progress was followed by collecting, in a trap of dry ice/acetone at −80° C., the $NH_3$ formed as reaction product. The yield in triazine A based on the reacted I-4 was 100%; 139 g of triazine A were indeed obtained. The yield was confirmed by the production of 7.15 ml of $NH_3$ (compared with the expected theoretic 7.18 ml). The conversion was 94.9%.

Spectroscopic analyses: FT-IR (NaCl): 1555 $cm^{-1}$; 1388 $cm^{-1}$; 1206+1140 $cm^{-1}$.

$^{19}$F-NMR (90 MHz); −58 ppm, S; −113.3 ppm, S; −116.5 ppm, s; −120.3 ppm, s; −125.6 ppm, s.

EXAMPLE 6 (triazine B)

Synthesis of 2,4,6-(1,1,2,2,3,3,4,4,5,5-decafluoro-7-iodoheptane)[1,3,5]triazine 90 g of triazine A obtained in the previous Example, equal to 45 cc (0.0745 moles) were introduced into a 300 cc AISI 316 autoclave.

It was homogeneously dissolved in 50 ml of acetonitrile. 2.45 g of CuI equal to 6% by moles of $Cu^+$ based on the triazine A moles were added. The autoclave was closed after having introduced a little magnetic rod and put in a thermostated oil bath at a temperature of 160° C. 0.447 moles of ethylene equal to a molar excess of 2:1 based on the three ethylenation sites were added; the ethylene was introduced at the temperature of the autoclave of 65° C. (pressure of 28 atmospheres inside the autoclave). The temperature was rised to 150° C. in 20 min and maintained at that temperature for 2 hours and then rised to 160° C. in 10 min. It was maintained at T=160° C. for 30 hours or until it was no longer noticed any consumption of ethylene (lowering of the pressure inside the autoclave).

At the end of the reaction the ethylene excess was allowed to leak and the autoclave was purged with a small amount of nitrogen. The autoclave content was decanted in a separatory funnel containing 200 ml $H_2O$ and ice. The organic phase separated or the bottom was collected. The solvent was evaporated at reduced pressure (26 mbar and 40° C.). 99 g of triazine B (formula II) powdered brown solid were obtained. The product can be decoloured to a powdered orange solid by active carbon suspended in an homogeneous solution of triazine B and acetonitrile. The yield in triazine B based on the reacted triazine A was 100% and the conversion is 93.1%.

Spectroscopic analyses: FT-IR (KBr): 2960 cm$^{-1}$; 1555.6 cm$^{-1}$; 565 cm$^{-1}$.

$^{19}$F-NMR (CH$_2$Cl$_2$): −114 ppm, S; −115.3 ppm, S; −119.6 ppm, s; −120.3 ppm, s; −122.4 ppm, s; −122.4 ppm, s.

EXAMPLE 7 (triazine C)

Synthesis of 2,4,6(1,1,2,2,3,3,4,4,5,5-decafluoro-hept-6-enyl)[1,3,5]triazine

An alcoholic solution of KOH (80 ml of ethanol and 10.13 g of KOH equal to 180.55 mmoles) was prepared; an alcoholic solution of triazine B obtained in the previous Example (275 ml of ethanol and 78.6 mmoles of triazine B equal to 182,37 mequivalents) was separately prepared; indifferently the triazine B/alcohol was dripped in the alcoholic solution of KOH or viceversa. The yields do not appreciably change, if one operates in the former or in the latter way. The flask containing the triazine B or the alcoholic solution of KOH was put in a bath at a T=54° C.

The maximum Exothermy reached was +5° C. The maximum pH reached during the reaction was 8–9 and the final pH, after a reaction time of 2 hours, was 6.5–7.5.

The reaction mixture was put in a separatory funnel, 500 ml of H$_2$O are added and it is extracted with 3 amounts of 100 ml of CH$_2$Cl$_2$. The organic phase was dried on MgSO$_4$ and was successively evaporated, after filtering MgSO$_4$, at a reduced pressure (26 mbar and 40° C.). The residual water and the ethanol were removed by azeotropic distillation by adding few ml of toluene to the organic solvent to be evaporated. 53 g of product were obtained, which looks as a viscous dark oil. The coloured impurities can be removed by means of suspended carbon in an homogeneous solution of triazine C/CH$_2$Cl$_2$. The yield in triazine C based on the reacted triazine B was 86% and the conversion was 75%.

The triazine C can be easily supported on CaSi$_2$O$_5$ in a percentage of 37.5% of triazine C and 62.5% of CaSi$_2$O$_5$.

Spectroscopic analyses: FT-IR : 1737 cm$^{-1}$; 1582 cm$^{-1}$; 1421 cm$^{-1}$; 1394 cm$^{-1}$; 1194+1134 cm$^{-1}$;

$^{19}$F-NMR (90 MHz; DMSO); −112.4 ppm, s; −116.4 ppm, s; −121.4 ppm, s; −122.4 ppm, s; −123.9 ppm, S.

$^{1}$H-NMR (200 MHz; DMSO$_{D6}$): 6.1 ppm, m.

We claim:
1. Triazines of formula

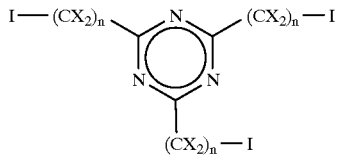

II wherein:

X can independently be hydrogen, chlorine, fluorine, C$_1$–C$_3$ alkyl or perfluoro alkyl, n is an integer ranging 2 and 20.

2. Triazines of formula

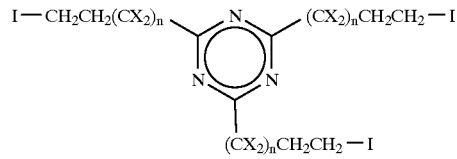

III wherein:

X can independently be hydrogen, chlorine, fluorine, C$_1$–C$_3$ alkyl or perfluoro alkyl, n is an integer ranging between 2 and 20.

* * * * *